United States Patent
Kiyota

(10) Patent No.: US 9,296,982 B2
(45) Date of Patent: Mar. 29, 2016

(54) CELL PICKING-ASSISTING DEVICE, DISPLAY DEVICE AND CULTURE CONTAINER

(75) Inventor: Yasujiro Kiyota, Tokyo (JP)

(73) Assignee: NIKON CORPORATION, Tokyo (JP)

( * ) Notice: Subject to any disclaimer, the term of this patent is extended or adjusted under 35 U.S.C. 154(b) by 1090 days.

(21) Appl. No.: 13/344,038

(22) Filed: Jan. 5, 2012

(65) Prior Publication Data

US 2012/0194664 A1 Aug. 2, 2012

Related U.S. Application Data

(63) Continuation of application No. PCT/JP2010/061585, filed on Jul. 8, 2010.

(30) Foreign Application Priority Data

Jul. 8, 2009 (JP) ................................ P2009-161437

(51) Int. Cl.
*H04N 7/18* (2006.01)
*C12M 1/00* (2006.01)
*C12M 1/34* (2006.01)
*C12M 1/36* (2006.01)

(52) U.S. Cl.
CPC ................ *C12M 23/50* (2013.01); *C12M 41/46* (2013.01); *C12M 41/48* (2013.01); *C12M 47/04* (2013.01)

(58) Field of Classification Search
CPC ...... C12M 23/50; C12M 41/46; C12M 41/48; C12M 47/04
USPC .......................... 348/79; 435/30, 287.1, 288.7
See application file for complete search history.

(56) References Cited

U.S. PATENT DOCUMENTS

| | | | | |
|---|---|---|---|---|
| 2005/0158846 | A1* | 7/2005 | Hibino et al. | 435/287.1 |
| 2009/0325280 | A1* | 12/2009 | Osawa et al. | 435/288.7 |
| 2010/0047902 | A1 | 2/2010 | Uozumi et al. | |
| 2011/0124037 | A1* | 5/2011 | Backhaus et al. | 435/30 |

FOREIGN PATENT DOCUMENTS

| | | |
|---|---|---|
| JP | 2004-248619 | 9/2004 |
| JP | 2005-326341 | 11/2005 |
| JP | 2007-330143 | 12/2007 |

(Continued)

OTHER PUBLICATIONS

Japanese Office Action issued Aug. 28, 2014 in corresponding Japanese Patent Application No. 2011-521952.

(Continued)

*Primary Examiner* — Allen Wong

(57) ABSTRACT

A cell picking support device, a display device and a culture container that can enhance work efficiency. An adapter fixes a well plate that holds cells cultured in a cell culture observation device. A control unit reads culture observation information that includes cell information and coordinate information, from a memory card that is fitted to an external memory I/F. A display unit is provided on a placing surface side of the well plate that is fixed by the adapter, and in response to control by the control unit, displays the cell information, read from the memory card, at display positions corresponding to positions on the bottom face of the well plate, as specified by the coordinate information. Embodiments can be used, for instance, as a cell picking support device that supports a picking operation that is performed in a clean bench.

9 Claims, 4 Drawing Sheets

(56) References Cited

FOREIGN PATENT DOCUMENTS

| | | |
|---|---|---|
| JP | 2007-330145 | 12/2007 |
| WO | WO 2007/001002 | 1/2007 |
| WO | 2008/034868 | 3/2008 |
| WO | 2009/031283 | 3/2009 |
| WO | 2009/050886 | 4/2009 |

OTHER PUBLICATIONS

Chinese Patent Office First Examination Written Argument Notification issued on Dec. 11, 2012 for corresponding Chinese Patent Application No. 201080030717.0.

International Search Report for PCT/JP2010/061585 mailed Aug. 10, 2010.

\* cited by examiner

CELL PICKING-ASSISTING DEVICE, DISPLAY DEVICE AND CULTURE CONTAINER

CROSS-REFERENCE TO RELATED APPLICATIONS

This is a continuing application, filed under 35 U.S.C. §111(a), of International Application PCT/JP2010/061585, filed Jul. 8, 2010, which claims priority benefit of Japanese Application No. 2009-161437, filed Jul. 8, 2009, which are incorporated herein by reference in their entireties.

BACKGROUND OF THE INVENTION

1. Field of the Invention

The present invention relates to a cell picking support device, a display device and a culture container.

2. Description of the Related Art

In recent years, pluripotent cells such as ES cells, iPS cells and the like have come to be cultured, in the form of, for instance, pure cultures where pluripotency characteristics are maintained, and cultures in which the cells are induced to differentiate into specific cells, in fields where regenerative medicine is pursued.

Such culture processes include selection of required cells or cell groups, and extraction of the cell or cell groups.

For instance, Japanese Patent Application Publication No. H10-293094 is an instance of a known method of testing this kind of cell data.

However, the operations of selecting and extracting cells according to a conventional method required checking the cells under the microscope. Operation efficiency was accordingly poor.

SUMMARY OF THE INVENTION

In the light of the above, it is an object of the present invention to allow enhancing work efficiency in a cell selection and extraction operation.

The cell picking support device of the present invention comprises: a fixing unit that fixes a culture container that holds cells cultured in a predetermined culture environment; an acquisition unit that acquires coordinate information for specifying positions, on a bottom face of the culture container, of specific cells from among the cells held in the culture container in the culture environment; and a display unit that is provided on a placing surface side of the culture container fixed by the fixing unit, and that displays information denoting the specific cells, at display positions corresponding to the positions on the bottom face of the culture container as specified by the coordinate information that is acquired by the acquisition unit.

The display device of the present invention is a display device that displays positions of target cells in a culture container in which cells are cultured, the display device comprising: a positioning unit that positions the culture container at a predetermined position on the display device; a position information acquisition unit that is disposed in the display device and that acquires position information on the target cells; and a display unit that displays, on the culture container, positions of the target cells.

A culture container of the present invention is a culture container in which cells are cultured, comprising: a container identification item that is provided in the culture container and that has specific information for specifying the culture container; and an alignment reference section that is formed outside a region in which the cells are present in the culture container, and that can be detected by a device on which the culture container is placed.

The present invention succeeds in enhancing work efficiency.

DESCRIPTION OF THE PREFERRED EMBODIMENTS

Embodiments of the present invention are explained below with reference to accompanying drawings.

Figure 1:
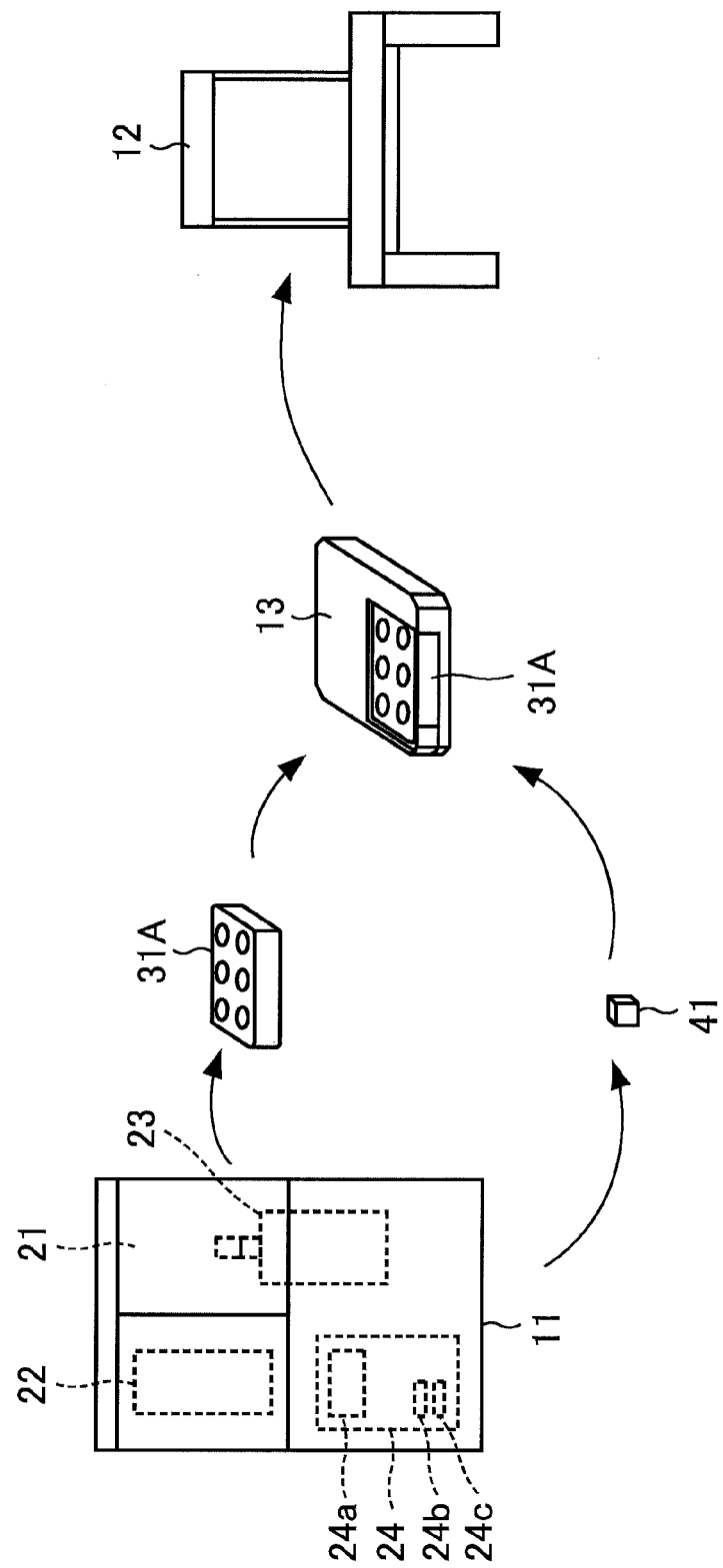
FIG. 1 is a diagram for explaining the gist of cell picking operation support of the present invention.

FIG. 1 is a diagram for explaining the gist of cell picking operation support of the present invention.

As illustrated in FIG. 1, a sample of cells or the like that are held in a well plate 31A is cultured in a cell culture observation device 11. In order to optimize, for instance, cell colony formation through seeding of such cells, some of the cells are picked up using a pipette (so-called picking) out of wells that are formed in the well plate 31A, and the picked colonies (cell aggregates) are transferred to another culture container (hereafter, picking operation).

This picking operation is ordinarily performed by conveying the well plate 31A to a clean bench 12 of FIG. 1 or a sterile room (not shown). Carrying out the picking operation in the clean bench 12 makes work possible in a sterile, dust-free environment. The culture container to which colonies have been transferred, as a result of the picking operation, is conveyed again to the cell culture observation device 11, and cell culture is resumed. The well plate 31A is a transparent member in which a plurality of concave culture reservoirs (wells) is arranged in order for cells to be cultured therein. A sample of cells or the like is held and is cultured in the wells.

A basic operation step of the picking operation has been explained above. The detailed configuration of the cell culture observation device 11 and a cell picking support device 13 of FIG. 1 is explained next.

In the cell culture observation device 11 of FIG. 1, solid lines denote the structure of portions that are visible from the outside, and broken lines denote the structure of internal portions that are not visible from the outside. A temperature-controlled chamber 21 covered by a heat-insulating material is formed inside a chassis at the top of the cell culture observation device 11. The interior of the temperature-controlled chamber 21 is sealed in order to maintain the cell culture environment during culture of the cells. Constant temperature, humidity or carbon dioxide concentration is maintained by way of a device for maintaining the interior environment, for instance a temperature-regulating device, a spraying device or a gas introduction unit provided inside the temperature-controlled chamber 21.

A stocker 22 and an observation unit 23 are housed in the temperature-controlled chamber 21. The stocker 22 is partitioned into a plurality of shelves, so that the well plate 31A can be held horizontally thereon.

The observation unit 23 is a device for observation of cells held in the well plate 31A that is conveyed in by a container transport mechanism (not shown). Herein, the cells are observed in accordance with two observation methods, namely phase contrast observation wherein cells are observed based on phase contrast of light that passes through the cells, and fluorescence observation wherein cells are observed by way of light resulting from excitation of fluorescent substances comprised in the cells. Images of light obtained during the above observations are captured by an imaging element such as a CCD (Charge Coupled Device), and the image signals are subjected to predetermined signal processing, to yield thereby an observation image of the sample, such as cells, that is cultured in the wells of the well plate 31A.

The control unit 24 performs a predetermined image analysis process on the observation images obtained by phase contrast observation in the observation unit 23, to extract as a result specific cells in the colony or the like, and calculates information (hereafter, coordinate information) for specifying the positions of specific extracted cells. That is, phase contrast observation allows visualizing and observing transparent cells. Therefore, specific cells in a colony or the like can be extracted by detecting the cells thus visualized from within the observation image. In the coordinate information, for instance, two-dimensional coordinates (x, y) for specifying the position of the extracted colony are calculated using one of the corners of a four-cornered well plate 31A, having a rectangular shape, as a reference point coordinate (hereafter, reference position).

Through performing a predetermined image analysis process on the observation image obtained by fluorescence observation in the observation unit 23, the control unit 24 extracts expressing cells from within the extracted colony, and acquires information (hereafter, cell information) relating to the type of the expressing cells. That is, expressing cells emit fluorescence of a predetermined color during fluorescence observation. Therefore, expressing cells can be extracted by detecting fluorescence from the observation image. The cell information is mapped to the above-described coordinate information, and hence presence or absence of expression at the position of the extracted colony can be determined for each colony. That is, calculating the above information items allows grasping whether or not a colony is present, and if so, whether the colony is an expressing colony or not.

The coordinate information and the cell information are mapped to identification information for uniquely identifying the culture container, such as the well plate 31A, and are recorded in a recording unit 24a. The identification information may be, for instance, bar codes (bar code 32b of FIG. 2 described below) that allow identifying respective culture containers accommodated in the stocker 22, and that are affixed to the side face of the culture container, such that the bar codes are acquired in accordance with a method that involves, for instance, reading by a bar code reader (not shown) that is disposed in the observation unit 23.

Through so-called time lapse observation, as a result, the cell information and coordinate information relating to samples held in respective wells of the well plate 31A and that are observed by the observation unit 23 are mapped to the identification information, and are sequentially stored, in a time series, in the recording unit 24a. The coordinate information and cell information mapped to the identification information will be referred to hereafter as culture observation information.

An external memory I/F 24b is an interface with a removable memory card 41. Culture observation information stored in the recording unit 24a is recorded in the memory card 41 that can be suitably fitted to the external memory I/F 24b, to make thus the information portable. The cell culture observation device 11 is provided with a communication unit 24c for performing communication according to a predetermined wireless or wired communication standard. The cell culture observation device 11 can thus exchange data with external devices, via a network. The cell culture observation device 11 can transmit, by way of a network, culture observation information to a device (cell picking support device 13 of FIG. 1) at a distant location.

In order to increase the work efficiency of the picking operation that is performed in the clean bench 12 as described above, the well plate 31A is fixed, in the present embodiment, to the cell picking support device 13, as illustrated in FIG. 1, and information and the like that denotes specific cells in a colony or the like is displayed, on the basis of the culture observation information that is obtained through fitting of the memory card 41, to support thereby the picking operation.

Figure 2:
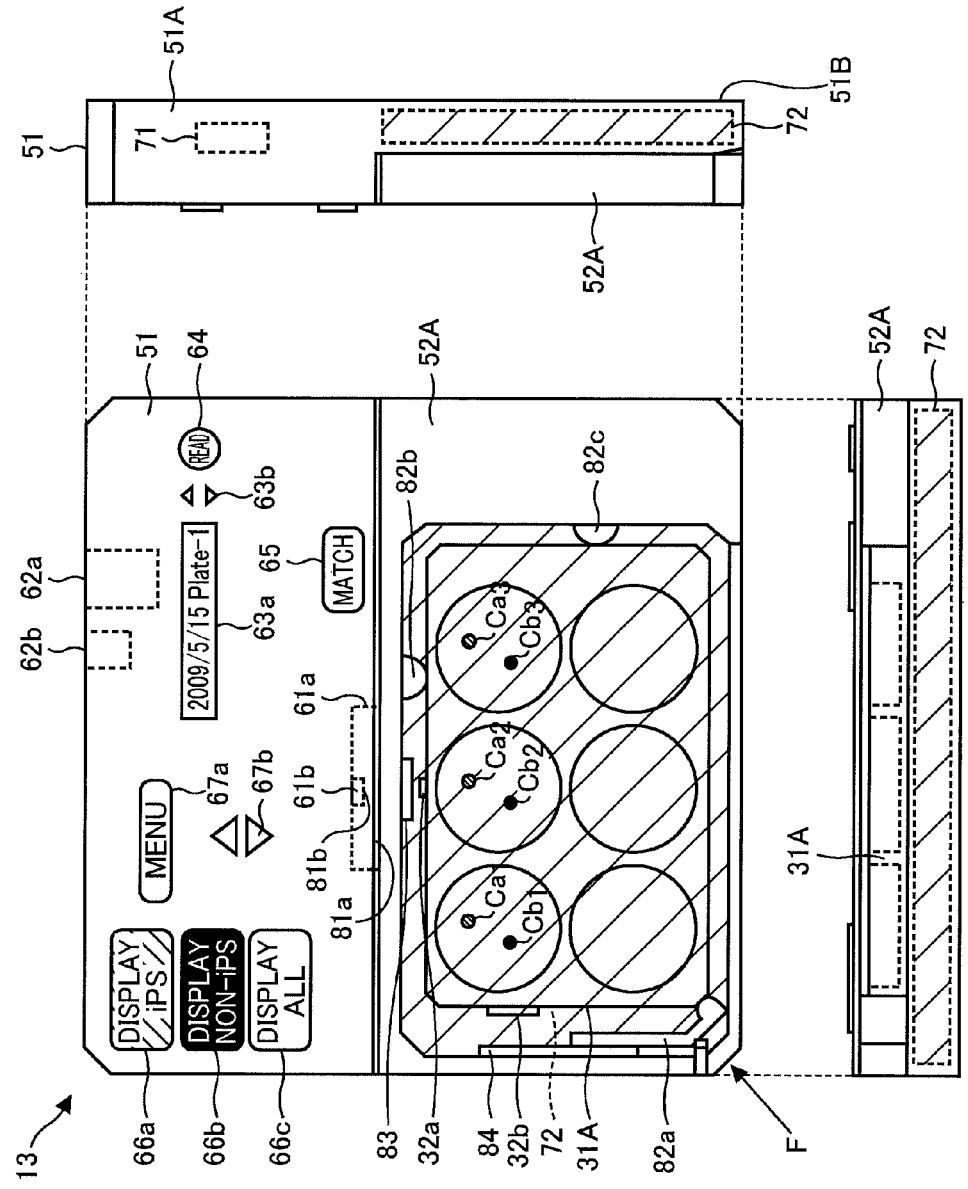
FIG. 2 is a diagram illustrating the configuration of an embodiment of a cell picking support device that utilizes the present invention.

FIG. 2 is a diagram illustrating the configuration of an embodiment of the cell picking support device that utilizes the present invention.

The cell picking support device 13 comprises a main body section 51, and an adapter 52A that is removably attached to the main body section 51. As illustrated in the side-view diagram, the main body section 51 is formed in such a manner that a main body chassis 51A and a display chassis 51B form substantially an L shape. A control unit 71 is disposed inside the main body chassis 51A, and a display unit 72, made up of an LCD (Liquid Crystal Display) or the like, is disposed in the display chassis 51B.

A fitting section 61a mechanically connected to the adapter 52A is provided, in the main body chassis 51A, at the connection surface with the adapter 52A. The main body section 51 and the adapter 52A become mechanically connected, and the adapter 52A becomes placed on the display chassis 51B, through fitting between the fitting section 61a and a fitting section 81a that is formed in the adapter 52A. A connector 61b provided in the fitting section 61a and a connector 81b provided in the fitting section 81a become electrically connected to each other upon mechanical connection between the main body section 51 and the adapter 52A. That is, the main body section 51 and the adapter 52A are configured so as to become electrically connected at the same time as they are mechanically connected.

Through electrical connection between the main body section 51 and the adapter 52A, a control signal is supplied to the adapter 52A, from the main body section 51 side, and predetermined information is supplied to the main body section 51 side, from the adapter 52A, via the connectors 61b, 81b. The main body section 51 and the adapter 52A may be fixed by virtue of the fitting force of the fitting sections 61a, 81a, or by using a fixing-jig, as the case may require.

The adapter 52A, has a shape corresponding to that of the well plate 31A, and is fixed to an outer peripheral portion of the side face of the well plate 31A by fixing members 82b, 82c. The lower left corner, in the figure, of the well plate 31A is pushed, in the direction of the fixing members 82b, 82c, by a fixing member 82a that comprises an elastic body having elastic force in the direction of arrow F. As a result, the well plate 31A becomes fixed to the adapter 52A. The well plate 31A fixed to the adapter 52A is placed on the display chassis 51B. Therefore, the operator can check information that traverses the well plate 31A, which is a transparent member, upon display of predetermined information by the display unit 72 that is arranged on the placing surface side of the display chassis 51B.

A position detection sensor 83 that reads an alignment mark 32a provided on the well plate 31A is disposed, in the adapter 52A, at the fixing face at which the well plate 31A is fixed. The alignment mark 32a is an item of information, for instance a seal inscribed with a predetermined mark, for unambiguously determining a positional relationship between the adapter 52A and the well plate 31A. Through positioning using the alignment mark 32a, one corner from among the four corners of the well plate 31A having a rectangular shape becomes fixed at a reference position, being a coordinate of a reference point in two-dimensional coordinates (x, y) that denote coordinate information. As a result, the position on the bottom face of the well plate 31A that is fixed by the adapter 52A can be determined by two-dimensional coordinates (x, y) that denote coordinate information calculated on the cell culture observation device 11 side.

A bar code reader 84 that reads the bar code 32b affixed to the well plate 31A is provided on the fixing face. The bar code 32b is an item of identification information for identifying uniquely the well plate 31A, and specifies the well plate 31A that is fixed, by the adapter 52A, from among the culture containers that are housed in the stocker 22 of the cell culture observation device 11. The bar code 32b is identical to the identification information that is read during observation in the observation unit 23 and that is mapped to coordinate information and cell information, as described above.

The information detected by the position detection sensor 83 and the bar code reader 84 is outputted from the main body section 51 side, via the connectors 81b, 61b, and is supplied to the control unit 71 that is provided in the main body chassis 51A.

An external memory I/F 62a, being a interface of the memory card 41 of FIG. 1, and a communication unit 62b for communication according to a predetermined wireless or wired communication standard, are provided in the main body chassis 51A of the main body section 51. The external memory I/F 62a reads culture observation information from an optionally fitted memory card 41, and supplies the information to the control unit 71. The communication unit 62b receives culture observation information, through communication with the cell culture observation device 11 of FIG. 1, via a network, and supplies the information to the control unit 71.

The main body chassis 51A comprises, as a user interface for operation setting of the cell picking support device 13: a container selection display unit 63a, a selection button 63b, a read button 64, a determination display unit 65, a first display button 66a, a second display button 66b, a third display button 66c, a menu button 67a and a selection button 67b.

Information corresponding to the information for specifying a culture container such as identification information comprised in the culture observation information, is displayed on the container selection display unit 63a. In accordance with an operation by the operator on the selection button 63b, there is selected a culture container for performing a picking operation from among the information (for instance, 2009/5/15 Plate-1, 2009/5/17 Plate-2, . . . ) that is displayed on the container selection display unit 63a.

When pressed by the operator, the read button 64 instructs the start of a determination process of whether a culture container that is selected by the container selection display unit 63a, and a culture container fixed to the adapter 52A, match each other or not. The determination result is displayed on the determination display unit 65. The text "match" is displayed on the determination display unit 65 when, for instance, the culture containers match, and "mismatch" is displayed when the culture containers do not match.

In response to an operation by the operator, the first display button 66a through the third display button 66c instruct display, on the display unit 72, of positions at which specific cells are present. Specifically, the first display button 66a instructs display of iPS cells (expressing cells). The second display button 66b instructs display of non-iPS cells (non-expressing cells), and the third display button 66c instructs display of cells that are both iPS cells and non-iPS cells.

The menu button 67a and the selection button 67b instruct various settings of the first display button 66a through third display button 66c. If, for instance, the menu button 67a is pressed in a state where the adapter 52A is removed from the main body section 51 and the entire display surface of the display unit 72 can be checked, a setting screen is displayed, on the display unit 72, for setting of the display contents of cell information of specific cells for which display is instruct by the first display button 66a through third display button 66c, as well as modifications in the display color or in the display method such as illumination, flashing or the like. Therefore, the above contents can be set through operation of the selection button 67b. In the present embodiment, thus, the assignment of the first display button 66a through third display button 66c is an example, and setting can be performed in an arbitrary manner.

The control unit 71 performs a cell picking operation support process through control of the operation of the various elements of the cell picking support device 13, on the basis of instructions that respond to operations performed by the operator, on the user interface.

Figure 3:
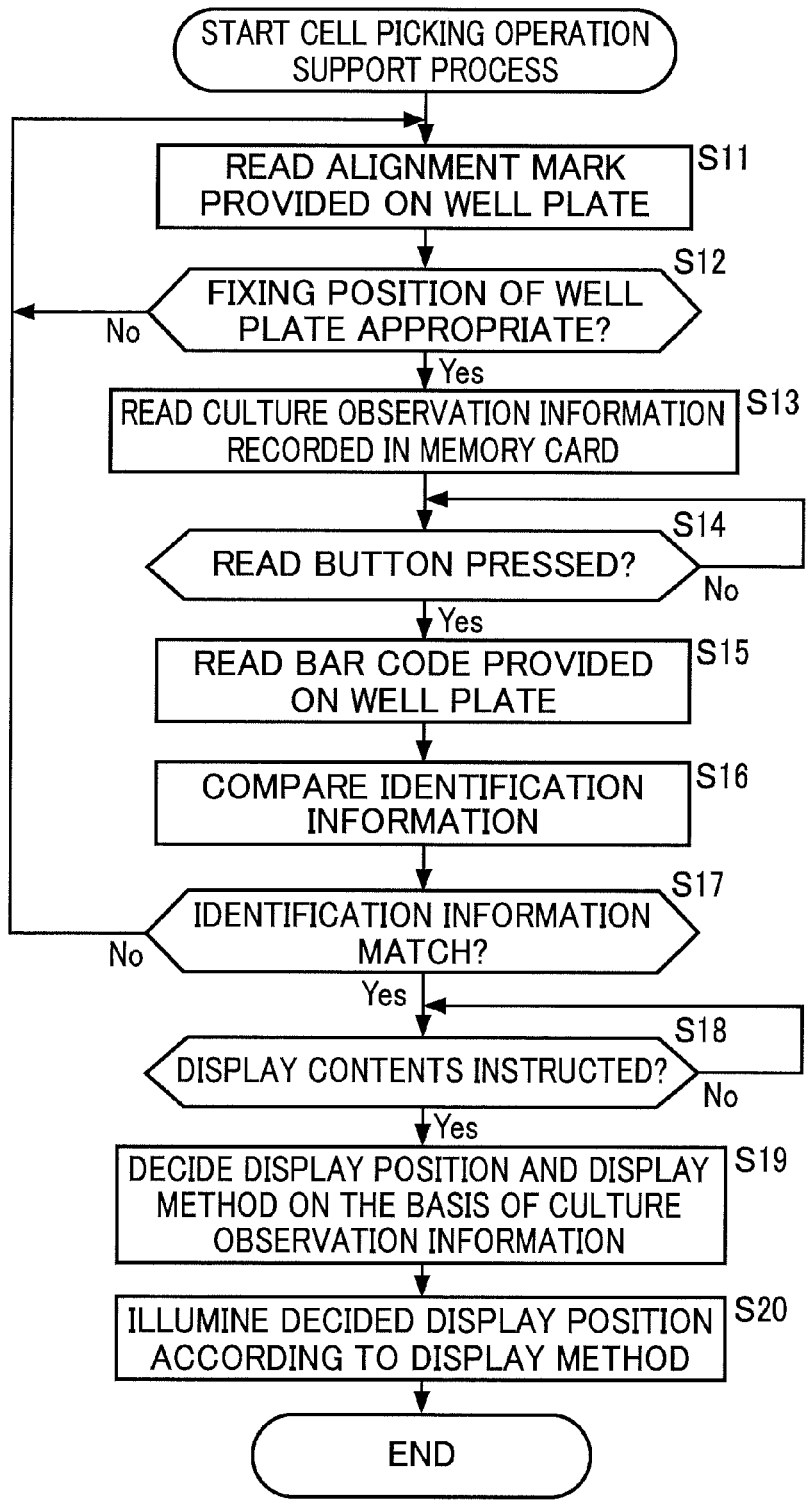
FIG. 3 is a flowchart for explaining in detail a cell picking operation support process.

A cell picking operation support process executed by the control unit 71 is explained in detail next with reference to the flowchart of FIG. 3.

Assuming that the present process is carried out in the cell culture observation device 11, a time lapse observation of the sample held in the well plate 31A is performed, and thereafter the well plate 31A is transported into the clean bench 12 of FIG. 1, and is fixed to the adapter 52A of the cell picking support device 13. The memory card 41 onto which there is recorded culture observation information that is obtained in the time lapse observation is fitted to the external memory I/F 62a. The desktop-type clean bench 12 has an operation space for observation of and experimentation with cells in a sterile, dust-free environment. Therefore, the operator introduces his/her hand through an opening provided in the side face of the clean bench 12, to perform thereby operations on the cell picking support device 13 that is disposed in the operation space.

In step S11, the position detection sensor 83 reads an alignment mark 32a provided on the well plate 31A that is fixed by the adapter 52A, and supplies the result to the control unit 71.

In step S12, the control unit 71 determines whether the fixing position of the well plate 31A is appropriate or not on the basis of the detection result of the alignment mark 32a by the position detection sensor 83. If in step S12 the fixing position of the well plate 31A is determined to be not appropriate, the control unit 71 issues a notification, by way of a notification unit such as the display unit 72, to the effect that fixing positioning of the well plate 31A has not been carried out correctly, and instructs the operator to re-fix the well plate 31A.

If in step S12 the fixing position of the well plate 31A is determined to be appropriate, then for instance one of the four corners of the well plate 31A has been fixed to a reference position, and hence the control unit 71 reads, in step S13, culture observation information that is recorded in the memory card 41 that is attached to the external memory I/F 62a, and in step S14, the control unit 71 determines whether the operator has pressed the read button 64.

If in step S14 it is determined that the operator has pressed the read button 64, the control unit 71 controls, in step S15, the bar code reader 84 so as to read the bar code 32b provided on the side face of the well plate 31A.

In step S16, the control unit 71 compares identification information denoted by the bar code 32b that is read by the bar code reader 84 and identification information comprised in the culture observation information that is acquired from the memory card 41 (identification information of the culture container selected by the container selection display unit 63a), and in step S17, determines whether or not the well plate 31A that is fixed to the adapter 52A matches the culture container selected by the container selection display unit 63a.

If in step S17 it is determined that the identification information does not match, then the culture container selected by the container selection display unit 63a is different from the well plate 31A that is fixed to the adapter 52A, and hence the culture container must be re-selected in the container selection display unit 63a, or the culture container fixed to the adapter 52A must be replaced. After these operations, therefore, the process returns to step S11, and the above-described process is executed again.

If in step S17 it is determined that the identification information matches, the process proceeds to step S18. The control unit 71 displays the text "match" on the determination display unit 65, and determines (process of step S18) whether display, on the display unit 72, of the positions at which specific cells are present, has been instructed or not through pressing of any of the first display button 66a through third display button 66c by the operator.

If in step S18 it is determined that display content has been instructed, the control unit 71 decides in step S19, on the basis of the culture observation information acquired from the memory card 41, display positions on the screen of the display unit 72 corresponding to the positions on the bottom face of the well plate 31A that are specified by the coordinate information of the specific cell for which display has been instructed, using the reference position as a reference point. The control unit 71 decides the display method, for instance, in what color the display positions are to be illuminated, on the basis of setting information that is set beforehand (display method set through operation of the menu button 67a). In step S20, the control unit 71 causes the decided display positions to be illuminated according to the display method. On the screen of the display unit 72, as a result, there is displayed information denoting specific cells, at display positions corresponding to positions on the bottom face of the well plate 31A that are determined by the two-dimensional coordinates (x, y) of the coordinate information, using the reference position as a reference point.

If, for instance, the first display button 66a is pressed, the control unit 71 decides the display positions on the screen of the display unit 72 as determined by the two-dimensional coordinates (x, y) of the coordinate information corresponding to the cell information that denotes iPS cells (expressing cells), using the reference position as a reference point, and causes the display positions to be illuminated in a predetermined color. As a result, cell positions $Ca_1$, $Ca_2$, $Ca_3$, corresponding to positions at which there are iPS cells in the sample held in the wells of the well plate 31A are illuminated in a predetermined color, such as yellow, on the display unit 72, as illustrated in FIG. 2. Similarly, if the second display button 66b is pressed, cell positions $Cb_1$, $Cb_2$, $Cb_3$, corresponding to positions at which there are non-iPS cells (non-expressing cells) in the sample held in the wells of the well plate 31A are illuminated in a predetermined color, such as red, on the display unit 72; and if the third display button 66c is pressed, cell positions $Ca_1$, $Ca_2$, $Ca_3$ and cell positions $Cb_1$, $Cb_2$, $Cb_3$, corresponding to positions at which there are both iPS cells and non-iPS cells, are illuminated in respective predetermined colors.

As a result, upon performing a picking operation in the clean bench 12, the operator presses the first display button 66a in the case, for instance, of a picking operation of iPS cells, whereupon the positions (cell positions $Ca_1$, $Ca_2$, $Ca_3$ in FIG. 2) of iPS cells are illuminated in yellow. The iPS cells can be picked reliably thereafter, at the illuminated positions, through picking using a pipette held in the hand that is introduced through the opening. The cells may be simply picked sequentially at the illuminated positions, without a need for checking microscope images, even if the iPS cells are numerous. A fast picking operation can be thus performed as a result.

In the present invention, as described above, the positions at which cells are picked during a cell picking operation can be indicated through illumination in a predetermined color. This allows the picking operation to be performed reliably and quickly while enhancing work efficiency.

Figure 4:
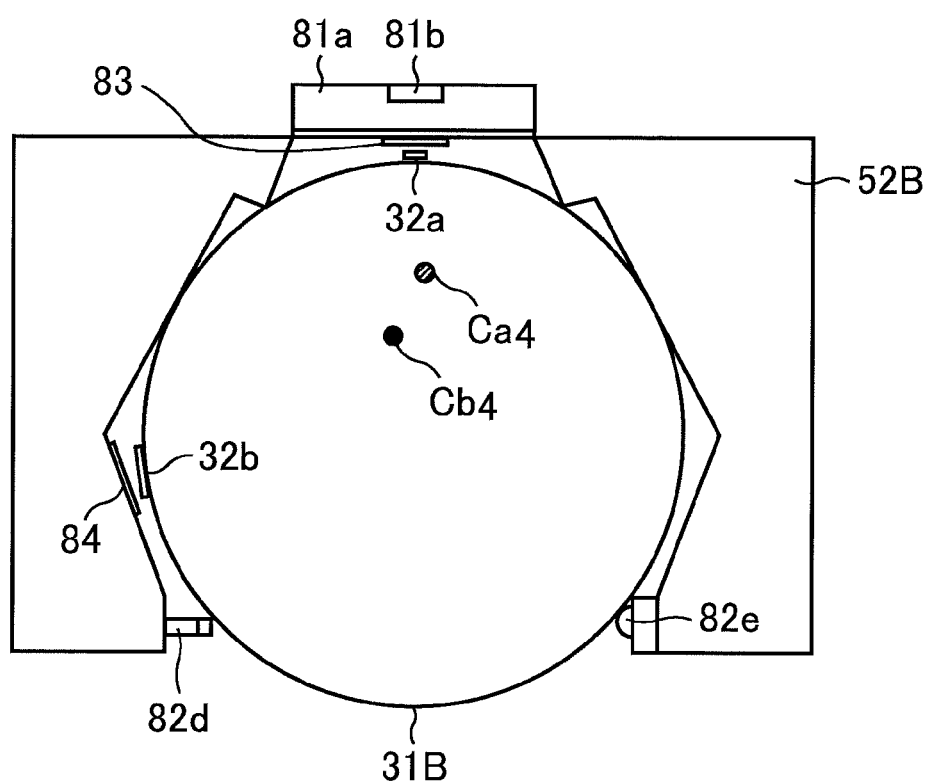
FIG. 4 is a diagram illustrating another configuration example of an adapter.

In the above description, the adapter 52A that is attached to the main body section 51 is removable, but for instance an adapter 52B illustrated in FIG. 4 may be attached instead of the adapter 52A.

The adapter 52B has a shape corresponding to that of a circular Petri dish 31B, such that the side face of the Petri dish 31B is fixed by way of fixing members 82d, 82e. As in the adapter 52A, the alignment mark 32a and bar code 32b provided on the Petri dish 31B can be read by the position detection sensor 83 and the bar code reader 84. The culture observation information acquired via the memory card 41 includes in this case cell information on cells held in the Petri dish 31B and that are subjected to culture observation in the cell culture observation device 11, as well as coordinate information on the cell information, mapped to identification information of the Petri dish 31B. On the basis of the above information items, the control unit 71 decides the display positions on the screen of the display unit 72 as determined by the two-dimensional coordinates (x, y) of coordinate information, using the reference position as a reference point, and displays, on the display unit 72, cell positions $Ca_4$, $Cb_4$ at which iPS cells and non-iPS cells are present, as illustrated in FIG. 4.

In the cell picking support device 13, thus, the adapter 52A that fixes the culture container is removably attached to the main body section 51, and can be replaced by an adapter that conforms to the shape of the culture container. Therefore, the cell picking operation can be supported regardless of the shape of the culture container.

In the explanation of the present embodiment, both phase contrast observation and fluorescence observation are performed upon acquisition of the culture observation information in the observation unit 23. However, fluorescence observation may be omitted, and just phase contrast observation be performed, in a case where information relating to expressing cells is not necessary and merely information relating to the presence or absence of colonies is to be obtained. Other than the above-described method that involves observing cells that emit fluorescence, by fluorescence observation, the method for extracting expressing cells may be, for instance, a method wherein the presence or absence of expression is detected on the basis of the shape of an extracted colony, by phase contrast observation.

In the present embodiment, the well plate 31A is positioned through detection of the alignment mark 32a by the position detection sensor 83. However, the alignment mark 32a and the position detection sensor 83 may be omitted, and, for instance, there may be fixed, to the reference position, a fixing position of one of the four corners of the well plate 31A at the time where the outer peripheral portion of the side face of the well plate 31A is fixed by the fixing members 82a, 82b, 82c, as illustrated in FIG. 2.

In the examples explained above, a bar code that denotes identification information is affixed to the culture container, but, needless to say, other configurations are possible. For instance, an IC chip having a built-in RF (Radio Frequency) tag in which identification information is recorded may be affixed, instead of the bar code, to the culture container, such that identification information in the IC chip is read wirelessly by a dedicated reader. Also, the position detection sensor 83 and the bar code reader 84 may be attached to the main body section 51 side, instead of the adapter 52A side. In this configuration, no information need be exchanged, and hence the connectors 81b, 61b need not be provided.

Some other recording medium, such as an optical disk or the like, may be used instead of the memory card 41. In this case, an interface corresponding to that recording medium is provided on the cell picking support device 13 side. Besides the above-described coordinate information, cell information and identification information, the culture observation information may further include, for instance, information that is useful on the cell picking support device 13 side, for instance operator information that indicates by whom the culture container is observed. The cell picking support device 13 is configured so as to be capable of accommodating a battery (not shown), for instance a lithium ion secondary battery or the like, to make the device portable, without wires.

In the present description, the steps in a program that is stored in a recording medium encompass not only a process that is executed in a time-series fashion, according to the order in which the process is written, but also processes that are executed not necessarily time-sequentially, but in parallel or separately.

Embodiments of the present invention are not limited to the above-described ones, and may accommodate various modifications without departing from the gist of the present invention.

What is claimed is:

1. A cell picking support device, comprising:
    a fixing unit that fixes a culture container that holds cells cultured in a predetermined culture environment;
    an acquisition unit that acquires coordinate information for specifying positions, on a bottom face of the culture container, of specific cells from among the cells held in the culture container in the culture environment; and
    a display unit that is provided adjacent to the bottom face of the culture container fixed by the fixing unit, and that displays information denoting the specific cells, at display positions corresponding to the positions on the bottom face of the culture container as specified by the coordinate information that is acquired by the acquisition unit.

2. The cell picking support device according to claim 1, wherein the acquisition unit further acquires cell information relating to states of the specific cells, and
    the display unit displays information denoting the states of the specific cells at the display positions, on the basis of the cell information acquired by the acquisition unit.

3. The cell picking support device according to claim 2, wherein first identification information for uniquely identifying the culture container is attached to the culture container, and second identification information for uniquely identifying the culture container is mapped to the coordinate information and the cell information, the cell picking support device further comprises:
    a reading unit that reads the first identification information attached to the culture container that is fixed by the fixing unit, and
    when the first identification information read by the reading unit matches the second identification information, the display unit displays information denoting the states of the specific cells at the display positions.

4. The cell picking support device according to claim 2, wherein the acquisition unit acquires the coordinate information and the cell information by way of a recording medium or a network.

5. The cell picking support device according to claim 1, wherein the fixing unit is removably attached to a main body section at which the display unit is provided, and is interchangeable in accordance with a shape of the culture container.

6. The cell picking support device according to claim 1, wherein an alignment mark for positioning of the fixing of the culture container by the fixing unit is provided on the culture container, and the cell picking support device further comprises:
    a detection unit that detects the alignment mark provided on the culture container; and
    a notification unit that, on the basis of detection results by the detection unit, notifies whether positioning of the fixing of the culture container by the fixing unit has been performed accurately or not.

7. A display device that displays positions of target cells in a culture container in which cells are cultured, the display device comprising:
    a positioning unit that positions the culture container at a predetermined position on the display device;
    a position information acquisition unit that is disposed in the display device and that acquires position information on the target cells; and
    a display unit that is provided adjacent to a bottom face of the culture container and that displays, on the culture container, the positions of the target cells.

8. The display device according to claim 7, further comprising:
    an identification unit that identifies the culture container, wherein the position information acquisition unit acquires position information on the target cells on the basis of identification information obtained by the identification unit.

9. A culture container in which cells are cultured, comprising:
    a container identification item that is provided in the culture container and that has specific information for specifying the culture container;
    an alignment reference section that is formed outside a region in which the cells are present in the culture container, and that can be detected by a device on which the culture container is placed; and
    a display unit that is provided adjacent to a bottom face of the culture container and that displays information denoting the cells.

* * * * *